United States Patent [19]

Hofmeister et al.

[11] Patent Number: 4,885,117
[45] Date of Patent: Dec. 5, 1989

[54] PROCESS FOR THE PREPARATION OF (Z)-17α-HALOVINYL STEROIDS

[75] Inventors: Helmut Hofmeister; Henry Laurent; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 84,042

[22] Filed: Aug. 11, 1987

[30] Foreign Application Priority Data

Aug. 11, 1986 [DE] Fed. Rep. of Germany ....... 3627154

[51] Int. Cl.$^4$ .............................................. C07J 1/00
[52] U.S. Cl. ............................................... 260/397.45
[58] Field of Search ........................ 260/397.45, 397.4

[56] References Cited

FOREIGN PATENT DOCUMENTS 0137434 4/1985 European Pat. Off. ..
0169515 1/1986 European Pat. Off. .

OTHER PUBLICATIONS

Chemical Abstracts 109(15): 129452x; 109(13): 1107406; 103(25): 215643t; 106(19): 156767y; 106(25): 207795r; 104(3): 17301n; 103(21): 178505b; 110(3): 18642k; 72(21): 111707s; 64: 12758d; 59: 7606e; 56: 12981h; 69(21): 87357t; 66(23): 105111c.
Louis F. Fieser and Mary Fieser, Steroids, 1959, pp. 583–585.
Journal of American Chemical Society, line 94, No. 26, pp. 9256–9258, Dec. 27, 1972.

Primary Examiner—Brian E. Hearn
Assistant Examiner—Andrew Griffis
Attorney, Agent, or Firm—Millen, White & Zelano

[57] ABSTRACT (Z)-17α-halovinyl steroids of general Formula I

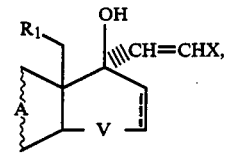

wherein
.... is a single bond or a double bond,
V is a carbon-to-carbon bond or a methylene group,
$R_1$ is a hydrogen atom or a methyl group,
X is a chlorine atom, a bromine atom or an iodine atom, and
A symbolizes the remainder of the steroid molecule, are prepared by hydrogenating a 17α-haloethynyl steroid of formula II with diimide.

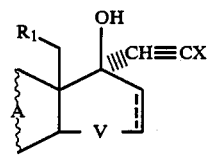

wherein ...., V, $R_1$, X and A have the meanings given above. The compounds of Formula I include both known and novel compounds, all of which are pharmacologically active.

4 Claims, No Drawings

PROCESS FOR THE PREPARATION OF (Z)-17α-HALOVINYL STEROIDS

BACKGROUND OF THE INVENTION

This invention relates to a process for production of (Z)-17α-halovinyl steroids and also to new halovinyl steroid compounds.

Similar compounds are disclosed in European Patent Applications Nos. 137,434 and 169,515 corresponding to U.S. Ser. Nos. 937,242 of Dec. 3, 1986 and 758,982 of July 25, 1985, respectively.

SUMMARY OF THE INVENTION

It is an object of this invention to provide a process for preparing (Z)-17α-halovinyl steroids which are pharmacologically active and thus useful in the preparation of medicaments and which also are useful as intermediates for the synthesis of radioactively labeled diagnostic agents.

Also, another object of this invention is to provide new (Z)-17α-halovinyl steroid compounds which are also pharmacologically active and useful as intermediates for synthesis of radioactively labeled diagnostic media in the same way as the previously known (Z)-17α-halovinyl steroids.

Upon further study of the specification and appended claims, further objects and advantages of this invention will become apparent to those skilled in the art.

These objects have been achieved by a process wherein (Z)-17α-halovinyl compounds of Formula I

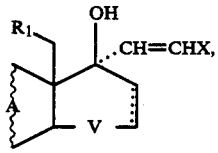

(I)

wherein

˙˙˙˙ is a single bond or a double bond,

V is a carbon-to-carbon bond or a methylene group, $R_1$ is a hydrogen atom or a methyl group, X is a chlorine atom, a bromine atom or an iodine atom, and A symbolizes the remainder of the steroid molecule, are prepared by hydrogenating a 17α-haloethynyl steroid of Formula II

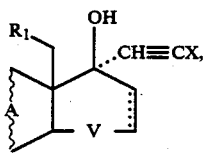

(II)

wherein ˙˙˙˙, V, $R_1$, X and A have the meanings given above.

The (Z)-17α-halovinyl steroids of general Formula I can be prepared in accordance with the above process in surprisingly high yields and with excellent purity. This process is performed under the conditions usually employed in the hydrogenation of compounds with diimide (Angew. Chem., 77: 368 et seq., 1965; J. Org. Chem. 49: 948 et seq., 1984, and 40: 1088, 1975; J. Amer. Chem. Soc., 94: 9256 et seq., 1972).

The diimide required for the reaction can be produced, for example, in a simple way by decomposition of the dipotassium salt of azodicarboxylic acid with weak acids (such as formic acid, acetic acid or oxalic acid). The dipotassium salt, in turn, is obtained by hydrolysis of azodicarboxylic acid diamide, azodicarboxylic acid dimethyl ester or azodicarboxylic acid diethyl ester with aqueous potassium hydroxide solution.

For purposes of the reaction, the dipotassium salt can be suspended, for example, in a lower alcohol (preferably methanol, ethanol or isopropanol) or in a polar ether (such as tetrahydrofuran, dioxane, glycol monomethyl ether or glycol dimethyl ether), the compound to be reacted can be added to the suspension, and then the reaction mixture can be acidified at a reaction temperature of about 0° C. to 80° C. Reaction times typically are about 5 to 120 minutes. The diimide is typically used in considerable excess, e.g., 3 to 20 moles per mole of steroid.

The starting compounds required for the reaction are known or can be synthesized analogously to the known compounds. See, e.g., U.S. Pat. No. 4,550,100 and the other publications cited herein.

In a preferred embodiment, the process of the invention can be used to prepare the (Z)-17α-halovinyl steroids of general Formula I wherein the remainder of the steroid molecule, A, represents a grouping having the partial formulas IIIa or IIIb

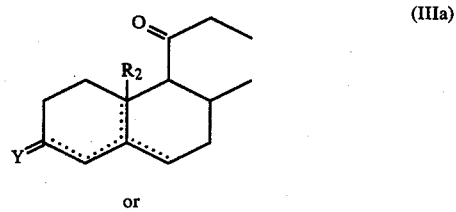

(IIIa)

or

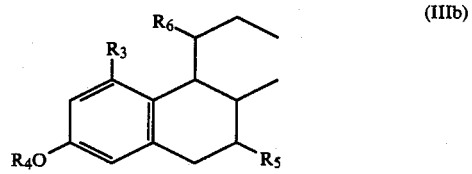

(IIIb)

wherein

˙˙˙˙ means single bonds or double bonds,

Y is an oxo group or an alkylenedioxy group of 2–6 carbon atoms or, in case the 3,4-linkage is a double bond, also symbolizes an alkoxy group, Z represents two hydrogen atoms or a methylene group, $R_2$ is a hydrogen atom or a methyl group, $R_3$ is a hydrogen atom, a hydroxy group, an alkoxy group of maximally 4 carbon atoms, or an alkanoyloxy group of maximally 4 carbon atoms, $R_4$ is a hydrogen atom, an alkyl group of maximally 4 carbon atoms, a 2-tetrahydropyranoyloxy group, or an alkanoyl group of maximally 4 carbon atoms, $R_5$ is a hydrogen atom or a methyl group, and $R_6$ is a hydrogen atom, an alkyl group of maximally 4 carbon atoms, or an alkoxy group of maximally 4 carbon atoms.

The (Z)-17α-halovinyl steroids of Formulas IIIa and IIIb can carry as the alkylenedioxy group Y, for example, an ethylenedioxy group, a 1,3-propylenedioxy group or a 2,2-dimethylpropylenedioxy group; or as the alkoxy group $R_3$ and/or $R_6$ a methoxy group, an ethoxy group, a propoxy group, a tert-butoxy group; or as the alkanoyloxy group $R_3$ an acetoxy group, a propionyloxy group, a butyryloxy group or a trimethylacetoxy group and/or as the alkyl group $R_4$ and/or $R_6$ a methyl group, an ethyl group, a tert-butyl group; or as the alkanoyl group $R_4$ an acetyl group, a propionyl group or a trimethylacetyl group.

In all of the above groups, the alkyl portions thereof are, for example, methyl, ethyl, isopropyl, n-propyl, isobutyl, n-butyl or tert.-butyl.

Some of the (Z)-17α-halovinyl steroids of general Formula I are known and are disclosed in European Patent Applications Nos. 137,434 and 169,515. These compounds are pharmacologically active and moreover represent valuable intermediates for the synthesis of radioactively labeled diagnostic agents. Other steroid compounds described by Formula I are novel. All compounds of formula I will have the same utility as the corresponding compounds devoid of halogen and are used analogously, e.g., in accordance with the details cited in the prior art disclosing such corresponding compounds. In addition, they have the same utility as do prior art halogenated steroids disclosed herein, especially those of U.S. Ser. No. 937,242.

The (Z)-17α-chlorovinyl steroids of general Formula Ia and the (Z)-17α-halovinyl steroids of general Formula Ib are novel.

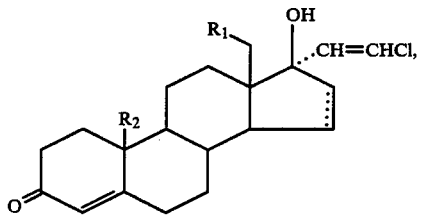

wherein

.... symbolizes a single bond or a double bond and $R_1$ and $R_2$ independently represent a hydrogen atom or a methyl group.

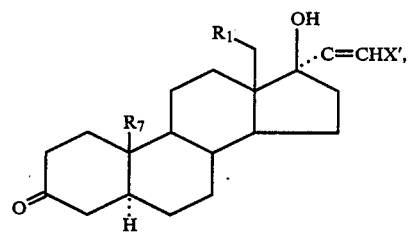

wherein $R_1$ and $R_7$ independently represent a hydrogen atom or a methyl group, and X' is a bromine atom or an iodine atom.

Like the known compounds of Formula I these novel steroids are active pharmacologically, having essentially the same spectrum of effectiveness as the corresponding compounds devoid of halogen and as the halogenated steroids disclosed herein, e.g., in U.S. Ser. No. 937,242. Moreover, these novel compounds can be converted into radioactively labeled diagnostic media in the same way as the previously known (Z)-17α-halovinyl steroids and used fully analogously.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, all temperatures are set forth uncorrected in degrees Celsius; unless otherwise indicated, all parts and percentages are by weight.

The entire text of all applications, patents and publications, if any, cited above and below are hereby incorporated by reference.

EXAMPLES

The examples set forth below serve for explaining the process of this invention in greater detail.

EXAMPLE 1

(a) At room temperature, 1.0 g of 17α-ethynyl-3,3-ethylenedioxy-5-estren-17β-ol in 20 ml of acetone is combined with 700 mg of N-iodosuccinimide and 50 mg of silver nitrate. After 30 minutes, the reaction mixture is diluted with ethyl acetate, washed with water, and dried. Chromatography on silica gel with a hexane/ethyl acetate gradient yields 790 mg of 3,3-ethylenedioxy-17α-iodoethynyl-5-estren-17β-ol, mp 123° C. (decomposition).

(b) At 0° C., 2.0 g of azodicarboxylic acid diamide is added under vigorous agitation to 2.4 g of potassium hydroxide in 6 ml of water. After 20 minutes, the precipitate is suctioned off, washed with 6 ml of cold methanol, and the salt is suspended in 10 ml of methanol. At room temperature, 200 mg of 3,3-ethylenedioxy-17α-iodoethynyl-5-estren-17β-ol is added to this suspension and then a mixture of 2 ml of glacial acetic acid and 6 ml of methanol is added dropwise thereto. After 15 minutes, the mixture is diluted with ethyl acetate, washed with water, and dried. After recrystallization from acetone/hexane, 110 mg of (Z)-3,3-ethylenedioxy-17α-(2-iodovinyl)-5-estren-17β-ol is obtained, mp 100° C. (decomposition).

(c) 2.0 g of (Z)-3,3-ethylenedioxy-17α-(2-iodovinyl)-5-estren-17β-ol is stirred under reflux in 40 ml of methanol and 4 ml of water with 2.0 g of oxalic acid. The reaction mixture is introduced into water after 30 minutes. The thus-precipitated product is suctioned off, dissolved in ethyl acetate, washed with water, and dried. After recrystallization from acetone/hexane, 1.5 g of (Z)-17β-hydroxy-17α-(2-iodovinyl)-4-estren-3-one is obtained, mp 125° C. (decomposition).

EXAMPLE 2

(a) Analogously to Example 1, 2.0 g of 17α-ethynyl-3,3-ethylenedioxy-18-methyl-5- and -5(10)-estren-17β-ol is reacted with N-iodosuccinimide and silver nitrate. Chromatography of the crude product with a hexane/ethyl acetate gradient yields 1.8 g of 3,3-ethylenedioxy-17α-iodoethynyl-18-methyl-5- and -5(10)-estren-17β-ol as a foam.

(b) As described in Example 1b, 800 mg of 3,3-ethylenedioxy-17α-iodoethynyl-18-methyl-5- and -5(10)-estren-17β-ol is reacted with diimide. The resultant, crude (Z)-3,3-ethylenedioxy-17α-(2-iodovinyl)-18-methyl-5- and 5(10)-estren-17β-ol is stirred under reflux for 30 minutes with 1.0 g of oxalic acid in 20 ml of methanol and 2 ml of water. The reaction mixture is poured into ice/water. The precipitated product is filtered off, dissolved in ethyl acetate, washed with water, and dried. After chromatography of the crude product on silica gel with a hexane/ethyl acetate gradient and recrystallization from acetone/hexane, 580 mg of (Z)-17β-hydroxy-17α-(2-iodovinyl)-18-methyl-4-estren-3-one is obtained as a foam.

EXAMPLE 3

Analogously to Example 1b, 3.4 g of 17α-iodoethynyl-3-methoxy-1,3,5(10)-estratrien-17β-ol (Angew. Chem. 1984: 720) is reacted with diimide. After chromatography of the crude product on silica gel with a hexane/ethyl acetate gradient and recrystallization from ether/hexane, 1.1 g of (Z)-17α-(2-iodovinyl-3-methoxy-1,3,5(10)-estratrien-17β-ol is obtained, mp 75° C. (decomposition).

EXAMPLE 4

Analogously to Example 1b, 450 mg of 3-benzoyloxy-17α-iodoethylnyl-1,3,5(10)-estratrien-17β-ol (Angew. Chem. 1984: 720) is reacted with diimide. After chromatography of the crude product on silica gel with a hexane/ethyl acetate gradient, 310 mg of (Z)-3-benzoyloxy-17α-(2-iodovinyl)-1,3,5(10)-estratrien-17β-ol is obtained, as an oil. The latter is dissolved in 10 ml of methanol and 1.2 ml of water and stirred at room temperature with 120 mg of potassium carbonate. After 60 minutes, the mixture is diluted with ethyl acetate, washed with water, and dried. Recrystallization from chloroform/hexane yields 133 mg of (Z)-17α-(2-iodovinyl)-1,3,5(10)-estratriene-3,17β-diol, mp 95° C. (decomposition).

EXAMPLE 5

(a) 2.7 g of 17α-ethynyl-3,3-ethylenedioxy-5α-androstan-17β-ol is combined with N-iodosuccinimide analogously to Example 1a. After recrystallization of the crude product from ethyl acetate, 2.8 g of 3,3-ethylenedioxy-17α-iodoethynyl-5α-androstan-17β-ol is obtained, mp 200° C. (decomposition).

(b) Analogously to Example 2b, 2.6 g of 3,3-ethylenedioxy-17α-iodoethynyl-5α-androstan-17β-ol is reacted to 1.1 g of (Z)-17β-hydroxy-17α-(2-iodovinyl)-5α-androstan-3-one, mp 96° C. (decomposition).

EXAMPLE 6

(a) Analogously to Example 1a, 2.0 g of 17α-ethynyl-3,3-ethylenedioxy-5-androsten-17β-ol is reacted with N-iodosuccinimide, thus isolating 1.9 g of 3,3-ethylenedioxy-17α-iodoethynyl-5-androsten-17β-ol as a foam.

(b) Analogously to Example 2b, 300 mg of 3,3-ethylenedioxy-17α-iodoethynyl-5-androsten-17β-ol is reacted to 180 mg of (Z)-17β-hydroxy-17α-(2-iodovinyl)-4-androsten-3-one, mp 107° C. (decomposition).

EXAMPLE 7

At 0° C., 29.5 g of azodicarboxylic acid diamide is introduced under vigorous agitation into 35.4 g of potassium hydroxide in 87 ml of water. After 20 minutes, the precipitate is suctioned off, washed with cold methanol, the salt is suspended in 148 ml of methanol, and 2.9 g of 17α-bromoethynyl-3-methoxy-1,3,5(10)-estratrien-17β-ol (Angew. Chem. 1984: 720) is added thereto. The mixture is combined dropwise with 29 ml of glacial acetic acid in 87 ml of methanol. The reaction mixture is introduced into ice/water. The thus-precipitated product is suctioned off, dissolved in methylene chloride, washed with water, and dried. Chromatography of the crude product with a hexane/acetone gradient on silica gel yields 2.0 g of (Z)-17α-(2-bromovinyl)-3-methoxy-1,3,5(10)-estratrien-17β-ol which is recrystallized from acetone/hexane, thus giving 1.7 g, mp 86° C. (decomposition)

EXAMPLE 8

(a) 3.0 g of 17α-ethynyl-3-(tetrahydropyran-2-yloxy)-1,3,5(10)-estratrien-17β-ol is reacted in 60 ml of acetone with 1.8 g of N-bromosuccinimide and 150 mg of silver nitrate at room temperature. After 30 minutes, the mixture is diluted with ethyl acetate, washed with water, and dried. After chromatography of the crude product on silica gel with hexane/ethyl acetate, 2.6 g of 17α-bromoethynyl-3-(tetrahydropyran-2-yloxy)-1,3,5(10)-estratrien-17β-ol is obtained as a foam.

(b) Analogously to Example 7, 2.4 g of 17α-bromoethynyl-3-(tetrahydropyran-2-yloxy)-1,3,5(10)-estratrien-17β-ol is reacted with diimide. Chromatography of the crude product on silica gel with a hexane/ethyl acetate gradient yields 1.8 g of (Z)-17α-(2-bromovinyl)-3-(tetrahydropyran-2-yloxy)-1,3,5(10)-estratrien-17β-ol as a foam.

EXAMPLE 9

(a) Analogously to Example 1a, 1.0 g of 17α-ethynyl-3,3-ethylenedioxy-18-methyl-5- and -5(10)-estren-17β-ol is reacted in 20 ml of acetone with 600 mg of N-bromosuccinimide and 50 mg of silver nitrate to 17α-bromoethynyl-3,3-ethylenedioxy-18-methyl-5- and -5(10)-estren-17β-ol. Yield: 920 mg as a foam.

(b) Analogously to Example 7, 500 mg of 17α-bromoethynyl-3,3-ethylenedioxy-18-methyl-5- and -5(10)-estren-17β-ol is reacted with diimide. The resultant crude product is stirred under reflux in 10 ml of methanol and 1 ml of water with 500 mg of oxalic acid. After 30 minutes, the reaction mixture is poured into ice/water, the thus-precipitated product is suctioned off, dissolved in ethyl acetate, washed with water, and dried. After chromatography of the crude product on silica gel with a hexane/ethyl acetate gradient, 210 mg of (Z)-17α-(2-bromovinyl)-17β-hydroxy-18-methyl-4-estren-3-one is obtained as a foam.

EXAMPLE 10

(a) At room temperature, 7.4 g of 17α-chloroethynyl-17β-hydroxy-18-methyl-4-estren-3-one [DAS 1,618,872 (1947)] is stirred in 74 ml of methylene chloride with 74 ml of ethylene glycol, 22 ml of trimethyl orthoformate and 120 mg of p-toluenesulfonic acid. After 3.5 hours, 4 ml of pyridine is added, the solution is concentrated under vacuum, and the residue is introduced into ice/water. The precipitated product is suctioned off, dissolved in methylene chloride, washed with water, and dried. After chromatography of the crude product on silica gel with a hexane/acetone gradient, 4.9 g of 17α-chloroethynyl-3,3-ethylenedioxy-18-methyl-5-estren-17β-ol is obtained, mp 182° C.

(b) Analogously to Example 7, 4.5 g of 17α-chloroethynyl-3,3-ethylenedioxy-18-methyl-5-estren-17β-ol is reacted with diimide. Chromatography of the crude product on silica gel with a hexane/ethyl acetate gradient yields 2.0 g of (Z)-17α-(2-chlorovinyl)-3,3-ethylenedioxy-18-methyl-5-estren-17β-ol, mp 102° C.

(c) 2.0 g of (Z)-17α-(2-chlorovinyl)-3,3-ethylenedioxy-18-methyl-5-estren-17β-ol is reacted analogously to Example 1c. After chromatography of the crude product on silica gel with a hexane/ethyl acetate gradient, 1.0 g of (Z)-17α-(2-chlorovinyl)-17β-hydroxy-18-methyl-4-estren-3-one is obtained as a foam.

EXAMPLE 11

(a) 4.0 g of 17α-chloroethynyl-17β-hydroxy-4-estren-3-one [U.S. Pat. No. 3,290,293 (1966)] is reacted analogously to Example 10a. Chromatography of the crude product on silica gel with a hexane/ethyl acetate gradient yields 3.1 g of 17α-chloroethynyl-3,3-ethylenedioxy-5- and -5(10)-estren-17β-ol as a foam.

(b) Analogously to Example 7, 2.5 g of 17α-chloroethynyl-3,3-ethylenedioxy-5- and -5(10)-estren-17β-ol is reacted with diimide. After chromatography on silica gel with a hexane/ethyl acetate gradient, 1.8 g of (Z)-17α-(2-chlorovinyl)-3,3-ethylenedioxy-5- and -5(10)-estren-17β-ol is produced as a foam.

(c) Analogously to Example 1c, 1.8 g of (Z)-17α-(2-chlorovinyl)-3,3-ethylenedioxy-5- and -5(10)-estren-17β-ol is reacted, yielding, after chromatography of the crude product with a hexane/ethyl acetate gradient, 950 mg of (Z)-17α-(2-chlorovinyl)-17β-hydroxy-4-estren-3-one, mp 97° C.

EXAMPLE 12

(a) 3.5 g of 17α-chloroethynyl-17β-hydroxy-18-methyl-4,15-estradien-3-one [DAS 2,636,405 (1976)] is reacted analogously to Example 10a. After chromatography of the crude product on silica gel with a hexane/ethyl acetate gradient, 2.8 g of 17α-chloroethynyl-3,3-ethylendioxy-18-methyl-5- and -5(10),15-estradien-17β-ol is isolated as an oil.

(b) Analogously to Example 7, 2.3 g of 17α-chloroethynyl-18-methyl-3,3-ethylenedioxy-5- and -5(10),15-estradien-17β-ol is reacted with diimide. Chromatography of the crude product on silica gel with a hexane/ethyl acetate gradient yields 1.6 g of (Z)-17α-(2-chlorovinyl)-3,3-ethylenedioxy-18-methyl-5- and -5(10),15-estradien-17β-ol as a foam.

(c) Analogously to Example 1c, 1.3 g of (Z)-17α-(2-chlorovinyl)-3,3-ethylenedioxy-18-methyl-5- and -5(10),15-estradien-17β-ol is reacted, yielding, after chromatography of the crude product on silica gel with a hexane/ethyl acetate gradient, 460 mg of (Z)-17α-(2-chlorovinyl)-17β-hydroxy-18-methyl-4,15-estradien-3-one as a foam.

EXAMPLE 13

(a) 1.9 g of 17α-ethynyl-3,3-ethylenedioxy-5α-estran-17β-ol is combined analogously to Example 1a with N-iodosuccinimide and silver nitrate, thus obtaining 2.0 g of 3,3-ethylenedioxy-17α-iodoethynyl-5α-estran-17β-ol as a foam. $[\alpha]_D^{20} = -18.6°$ (b) Analogously to Example 2b, 2.4 g of 3,3-ethylenedioxy-17α-iodoethynyl-5α-estran-17β-ol is reacted to 1.2 g of (Z)-17α-hydroxy-17α-(2-iodovinyl)-5α-estran-3-one, mp 100° C. (decomposition).

EXAMPLE 14

(a) 2.0 g of 17α-ethynyl-3,3-ethylenedioxy-5α-estran-17β-ol is reacted analogously to Example 8a in acetone with N-bromosuccinimide and silver nitrate, thus obtaining 2.1 g of 17β-bromoethynyl-3,3-ethylenedioxy-5α-estren-17β-ol as a foam.

(b) 800 mg of 17α-bromoethynyl-3,3-ethylenedioxy-5α-estran-17β-ol is reacted analogously to Example 9b with diimide and then treated with oxalic acid in a methanol-water mixture, yielding 380 mg of (Z)-17α-(2-bromovinyl)-17β-hydroxy-5α-estran-3-one as a foam.

EXAMPLE 15

(a) 600 mg of 17α-ethynyl-3,3-ethylenedioxy-5α-androstan-17β-ol is reacted analogously to Example 8a with N-bromosuccinimide and silver nitrate, thus obtaining 580 mg of 17α-bromoethynyl-3,3-ethylenedioxy-5α-androstan-17β-ol as a foam.

(b) 500 mg of 17α-bromoethynyl-3,3-ethylenedioxy-5α-estran-17β-ol is reacted analogously to Example 9b with diimide and then treated with oxalic acid in methanol-water, yielding 260 mg of (Z)-17α-(2-bromovinyl)-17β-hydroxy-5α-androstan-3-one as a foam.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A (Z)-17α-chlorovinyl steroid of the formula

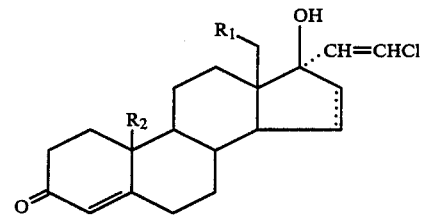

wherein

⋯ symbolizes a single bond or a double bond and $R_1$ and $R_2$ independently represent H or methyl.

2. (Z)-17α-(2-chlorovinyl)-17β-hydroxy-4-estren-3-one, of claim 1.

3. (Z)-17α-(2-chlorovinyl)-17β-hydroxy-18-methyl-4-estren-3-one, of claim 1.

4. (Z)-17α-(2-chlorovinyl)-17β-hydroxy-18-methyl-4,15-estradien-3-one, of claim 1.

* * * * *